United States Patent [19]

Preikschat

[11] 3,992,665
[45] *Nov. 16, 1976

[54] ELECTRICAL IMPEDANCE MEASURING APPARATUS

[76] Inventor: Fritz K. Preikschat, 16020 Lake Hills Blvd., Bellevue, Wash. 98008

[ * ] Notice: The portion of the term of this patent subsequent to July 16, 1991, has been disclaimed.

[22] Filed: June 26, 1974

[21] Appl. No.: 483,094

Related U.S. Application Data

[62] Division of Ser. No. 395,736, Sept. 10, 1973, Pat. No. 3,824,461, which is a division of Ser. No. 229,133, Feb. 24, 1972, Pat. No. 3,781,671.

[52] U.S. Cl............................................. 324/57 R
[51] Int. Cl.² ...................................... G01R 27/00
[58] Field of Search ......... 324/61 R, 61 QS, 61 QL, 324/65 R, 57 R

[56] References Cited
UNITED STATES PATENTS

| | | |
|---|---|---|
| 2,204,196 | 6/1940 | Straatman..................... 324/61 QS |
| 3,081,429 | 3/1963 | Moe................................ 324/61 R |
| 3,566,260 | 2/1971 | Johnston........................ 324/61 R |
| 3,691,457 | 9/1972 | Kriellaars..................... 324/61 R |
| 3,731,187 | 5/1973 | Hausler et al................. 324/65 R |
| 3,761,810 | 9/1973 | Fathauer....................... 324/61 R |
| 3,794,911 | 2/1974 | Fathauer....................... 324/61 QS |

*Primary Examiner*—Stanley T. Krawczewicz
*Attorney, Agent, or Firm*—Graybeal, Barnard & Uhlir

[57] ABSTRACT

Apparatus for measuring the electrical impedance of a variety of materials including an electrode arrangement providing sample data to an impedance bridge, a frequency generator providing a test signal to the impedance bridge, the impedance bridge including a transformer having three separate windings, two of which are highly symmetrical to each other and all three of which have an impedance below 10,000 ohms, and four resistors having resistance values differing from the impedance of the transformer windings but comparable to the unknown impedance, two of the four resistors connected to each of the two symmetrical windings of the transformer. Output devices for displaying the electrical impedance are also disclosed. In one embodiment, a sample box useful in the measurement of the electrical impedance of bulk materials including novel means for mounting an electrode therein is disclosed. Also disclosed in another embodiment is apparatus useful for measuring the electrical impedance of thin sheet material including novel mechanical thermal compensation means.

13 Claims, 12 Drawing Figures

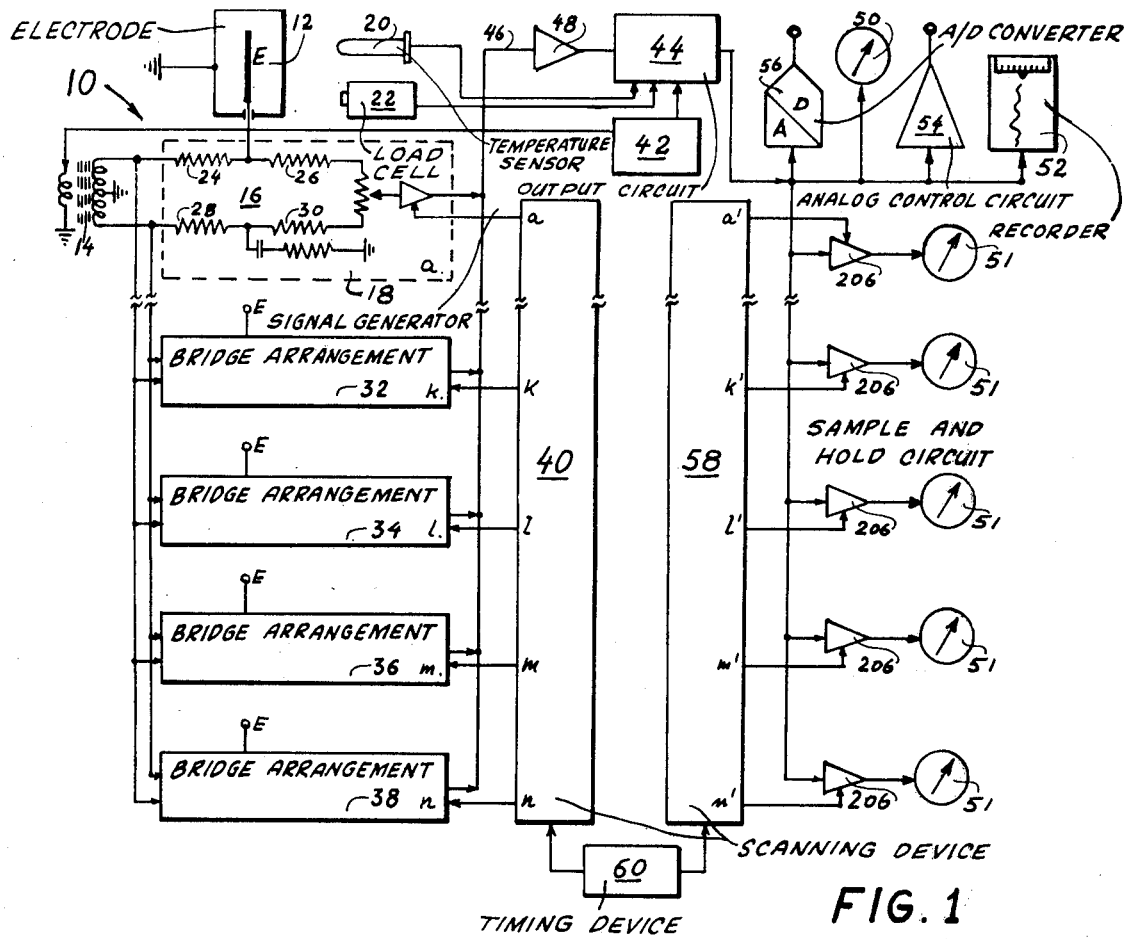
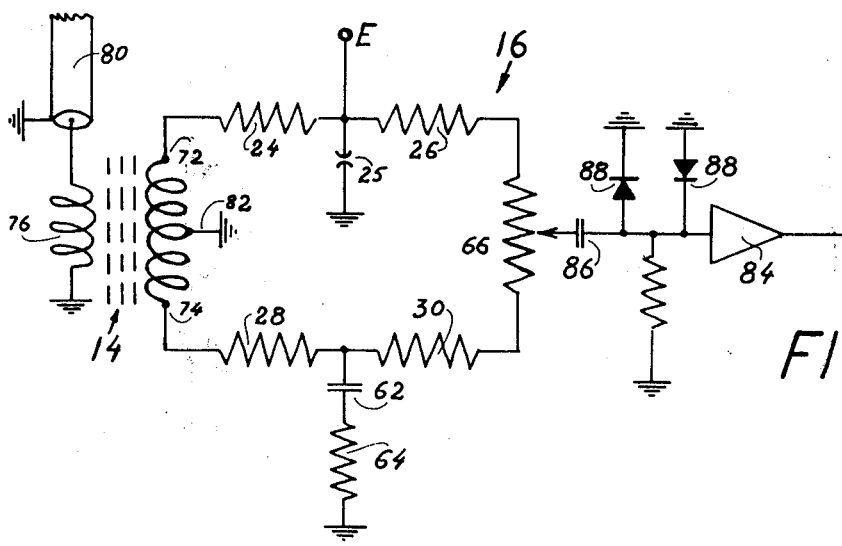
FIG. 1
FIG. 2.

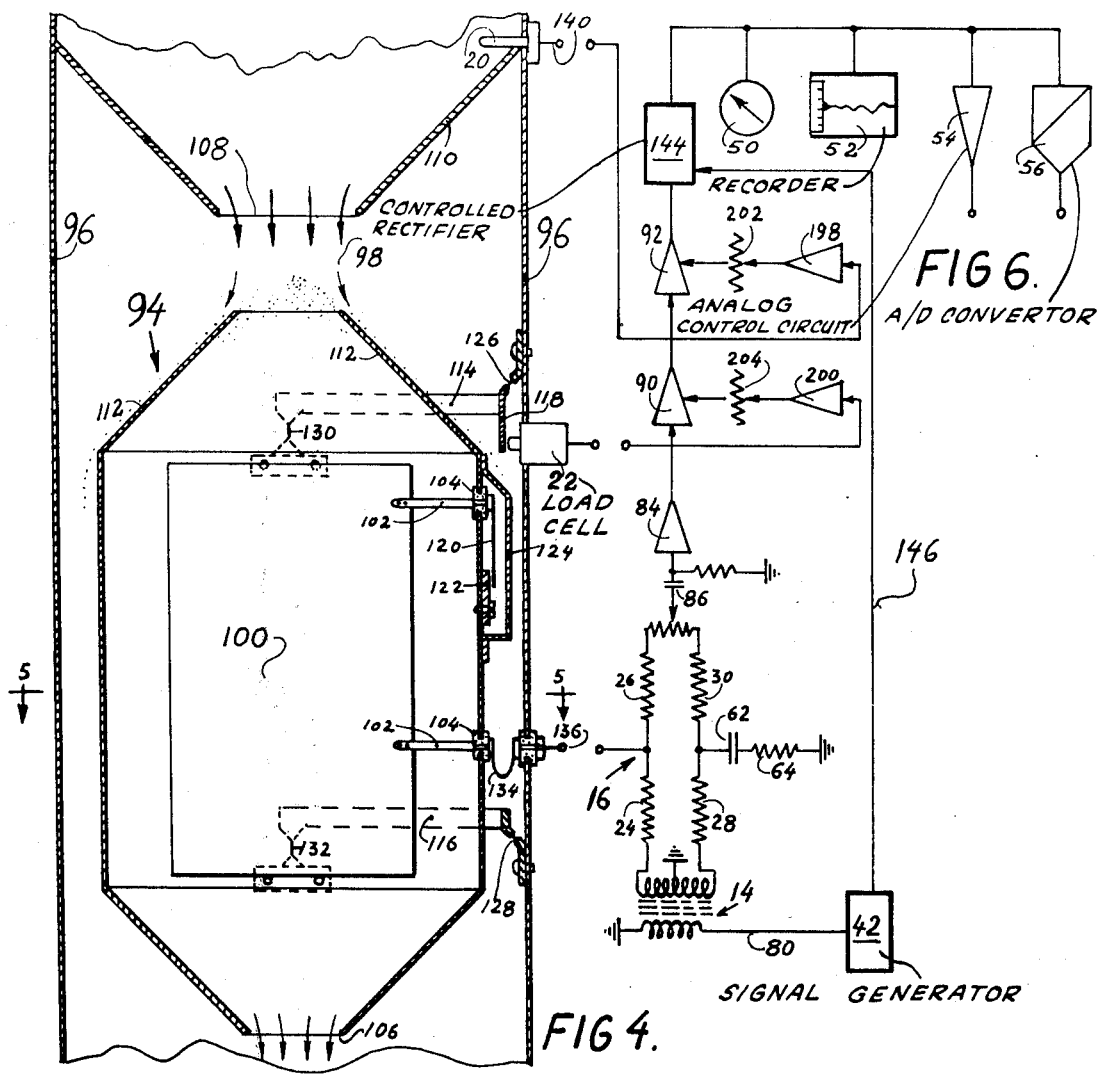
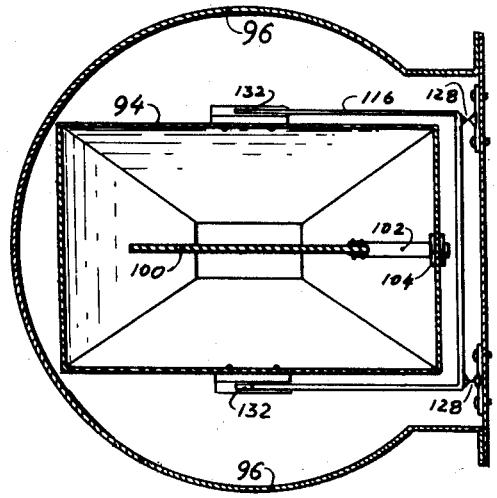
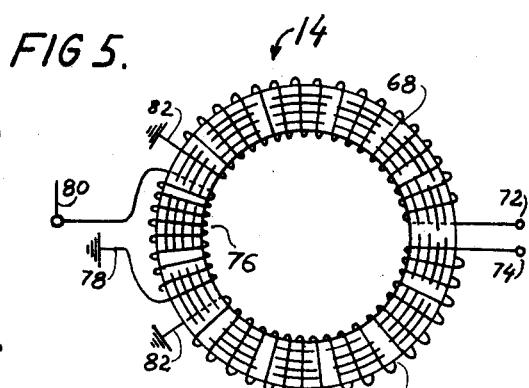

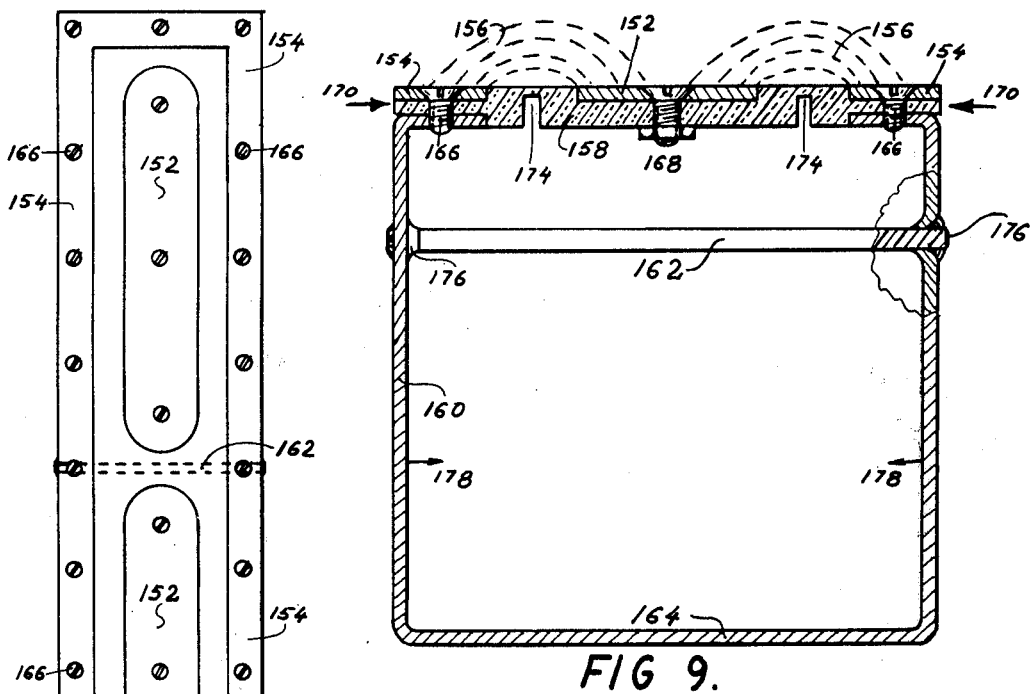
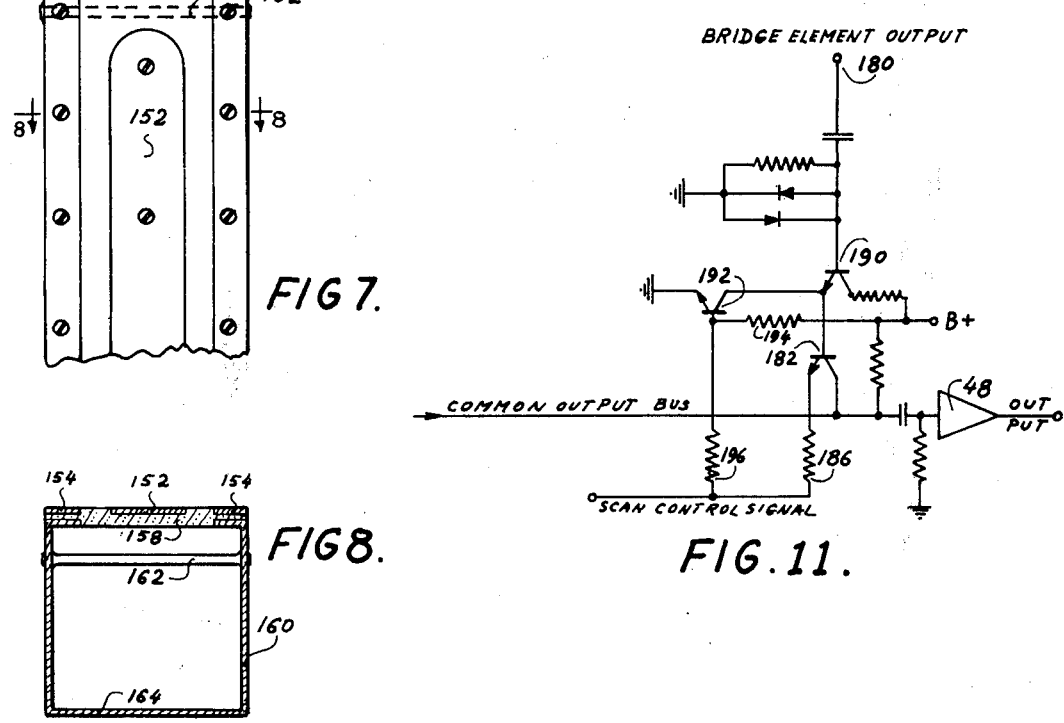

ELECTRICAL IMPEDANCE MEASURING APPARATUS

CROSS-REFERENCE TO RELATED APPLICATIONS

This is a division of my copending application Ser. No. 395,736 filed 9/10/73, now U.S. Pat. No. 3,824,461 issued July 16, 1974 entitled Electrical Impedance Measuring Apparatus, which application is a division of my prior application Ser. No. 229,133, filed Feb. 24, 1972 entitled Impedance Measuring Bridge Circuit and which issued as U.S. Pat. No. 3,781,671 on Dec. 25, 1973.

BACKGROUND OF THE INVENTION

1. Field of the Invention

This invention relates to apparatus for measuring the electrical impedance of materials, and in particular relates to apparatus for measuring the electrical impedance of a given volume or area of sample material and relating this impedance to a particular characteristic of the material such as moisture content.

2. Description of the Prior Art

Optimization of the yield of various manufacturing processes often requires very accurate monitoring of the moisture content of a given material. For example, the milling of wheat is carried on most efficiently when the wheat has a 15% moisture content. During the pulping of wood chips, the moisture content of the wood chips must be known in order to determine the proper amounts of liquor necessary to be added for maximum delignification. The required accuracy for the measurement of moisture varies for different materials and is shown below for some representative materials:

| Material | Moisture Range | Required Accuracy of Moisture and Indication | Percent of Full Scale |
|---|---|---|---|
| Wood Chips | 30%–70% | ± 3% | ± 7% |
| Wheat | 8%–15% | ± 0.2% | ± 1.4% |
| Paper | 5%–10% | ± 0.5% | ± 5% |
| Plywood Veneer | 3%–8% | ± 0.5% | ± 6% |
| Potato Chips | 12%–17% | ± 0.5% | ± 3% |

The most exacting measurement requires an accuracy of 1.4% of full scale.

Known moisture measuring systems for the above listed materials have, in general, proved unreliable for a variety of reasons including the instability of the bridge circuitry used to measure the electrical impedance of samples and the failure of the known systems to compensate for changes in temperature and density of the material, both of which critically affect the measurement of impedance. While the impedance reading may be compensated for these variations under laboratory conditions, no practical system is known for making the necessary corrections while measuring impedance "on-line" as is required for continuous process control.

Known moisture detection apparatus include those described in U.S. Pat. No. 3,391,337 and U.S. Pat. No. 3,430,140, which patents list applicant as inventor.

The degree of accuracy necessary for accurate moisture content measurement may be illustrated by noting that to determine the moisture content of wheat having a moisture content of between 8% and 15% with an accuracy of ± 0.2%, i.e., an absolute accuracy of about 1.5% of the full scale measurement, all critical components of the moisture meter must remain constant to within about ± 0.1% so as not to contribute a total accumulated error of more than one half of the desired accuracy. A 25 cubic inch sample of wheat having a 10% moisture content has an impedance with an ohmic component of about 100,000 ohms and a capacitive component of about 30 picofarads. A small change in moisture content may only be measured accurately if the impedance bridge components of the moisture content measuring meter are constant with respect to thermal drift and aging to an accuracy of at least 0.01 picofarads.

Temperature variations may also considerably influence the impedance of a sample material. Impedance of wood chips, for example, changes by a factor of 2 for a 40° C. change above the freezing point. In addition, a discontinuity in impedance exists at the freezing point and the rate of change in impedance below the freezing point is drastically different. Consequently, a meter which is effective for measuring the moisture content of a material must have a built-in temperature correction capability capable of correcting for aberrations in impedance existing over a wide temperature range.

In measuring the moisture content of bulk materials, density is another critical factor. For a bulk sample having a constant moisture content, impedance varies inversely with density. One possible way of correcting moisture measurement for variations in density involves the measuring of samples of constant weight. It has been found, however, that the moisture reading of a sample is not exactly proportional to the inverse bulk density of the sample and thus this method requires the use of additional calibration charts in order to produce a usable reading. A second technique for compensating for variations in density involves constant volume sampling, and this technique has been found to be more reproducible and versatile in that the weight of a sample of constant volume may be directly measured and introduced as a corrective factor in the ultimate moisture content measurement.

BRIEF SUMMARY OF THE INVENTION

The present invention discloses apparatus for measuring moisture content of a variety of materials by accurately measuring the electrical impedance of sample portions of the material. The apparatus includes sensing electrodes of particular geometry arranged with regard to the nature of the material sampled feeding to an impedance bridge circuit having an inherent stability of approximately one part in ten thousand. The bridge circuitry includes a unique transformer arrangement of great stability, and the apparatus additionally includes means for compensating for variations in temperature and density of the sampled material. In one embodiment for sampling bulk material, a unique system for supporting a sample box and an electrode disposed therein is disclosed. In another embodiment related to the sensing of the moisture content of sheet material, mechanical means for compensating for temperature variation is disclosed.

It is an object of this invention, therefore, to provide an impedance measuring system which is inherently stable and in which the aging and thermal drift of critical components is negligible.

Another object is to provide an impedance measuring system capable of measuring the temperature and density of the sample material and compensating the primary impedance reading for variations in these parameters.

One more object is to provide unique electrode configurations for a moisture measuring system whereby the moisture content may be measured in materials which differ not only in their electrical but also in their physical characteristics.

Still another object is to provide a moisture measuring system including temperature and density compensating components whereby the moisture measurement may be made on a continuing basis for direct "on-line" control or on a discontinuous basis for a batch flow system.

A more specific object of the present invention is to provide a moisture measuring system including a plurality of electrodes connected in parallel and operated consecutively in time using the same circumferential circuitry to measure moisture content incrementally across a wide sheet of material.

A related object is to provide mechanical temperature compensation means for a moisture measuring system for a wide sheet of material.

Another specific object is to provide novel means for supporting a continuous flow sample box, and for supporting a sensing electrode within the continuous flow sample box.

Still another object is to provide impedance bridge circuitry of exceptional stability.

Other and additional objects and advantages of the present invention will be apparent from the following description, taken in conjunction with the accompanying drawings.

BRIEF DESCRIPTION OF THE DRAWINGS

FIG. 1 is a schematic diagram of a typical impedance measuring apparatus made according to the instant invention.

FIG. 2 is a schematic circuit diagram of a typical bridge arrangement made according to the instant invention.

FIG. 3 is a schematic plan view of a typical bridge transformer made according to the instant invention.

FIG. 4 is a cross sectional elevation view of a typical sample box made according to the instant invention for use in conjunction with bulk materials.

FIG. 5 is a section view taken along lines 5—5 of FIG. 4.

FIG. 6 is a schematic diagram of a typical moisture measuring apparatus made according to the instant invention for use in conjunction with the sample box of FIG. 4.

FIG. 7 is a partial plan view of a typical electrode array made according to the instant invention useful in conjunction with the measuring of the moisture content of a thin web of material.

FIG. 8 is a section view taken along lines 8—8 of FIG. 7.

FIG. 9 is an enlarged detail view of the cross section of FIG. 8, including the electric fields shown in dashed line.

FIG. 11 is a schematic diagram of a switching circuit made according to the instant teaching having low leakage current which may be used in conjunction with a plurality of sensing electrodes.

DETAILED DESCRIPTION OF THE INVENTION

Figure 10:
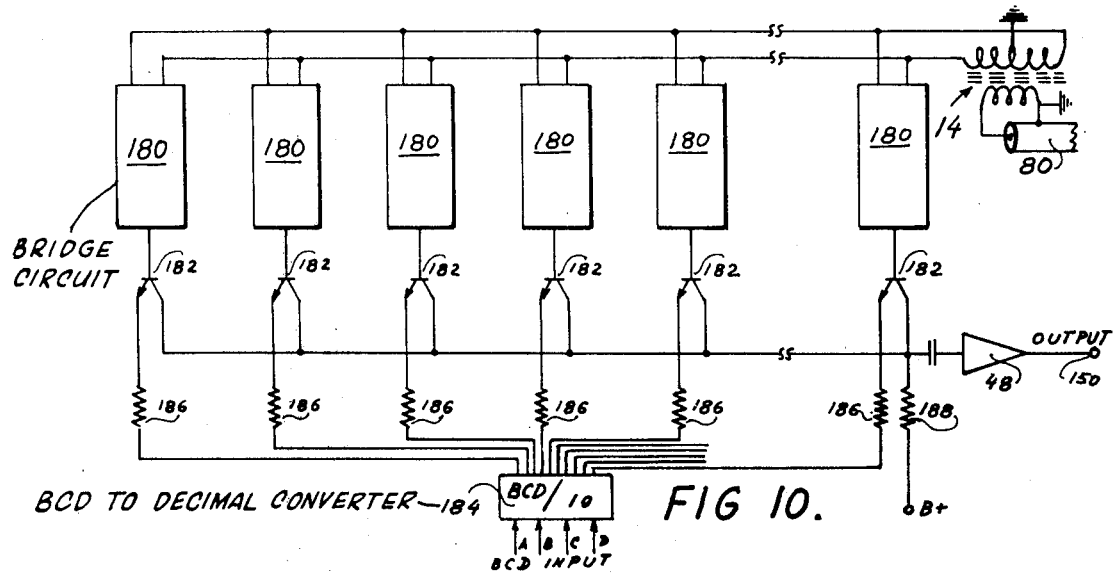
FIG. 10 is a schematic diagram of a typical bridge arrangement according to the instant invention including a plurality of sensing electrodes.

Referring initially to FIG. 1, an apparatus and support circuitry 10, made according to the teachings of the instant invention for sampling the impedance of a material is disclosed, including sensing electrode arrangement 12, transformer 14, bridge circuitry 16 shown within dashed line 18, temperature sensor 20 and bulk density sensor 22. The impedance of a sample of material is measured in a high frequency field generated by electrode arrangement 12 which may be of varying geometry depending upon the nature and configuration of the material to be measured. For example, FIG. 4 discloses an electrode arrangement useful for measuring the impedance of bulk materials, while FIG. 7 discloses an electrode arrangement useful for measuring the impedance of sheet materials. As disclosed, electrode 12 is interconnected with bridge circuit 16 which includes resistors 24, 26, 28 and 30. The impedance of the sample material is determined through the use of the disclosed apparatus by measuring its impedance between the electrode and ground.

FIG. 1 additionally discloses a plurality of bridge arrangements represented by lined boxes 32, 34, 36 and 38 and their associated sensing electrodes E arranged to be interconnected with each other and with bridge circuitry 16 to measure impedance across a wide, flat area of test material such as a web of paper or the like. When used in this mode, a conventional scanning mechanism 40 is employed to consecutively and repeatedly sample the outputs of all bridges in the array. In actual practice, the bridge assemblies are usually located in a strategic position close to the material to be sampled while the remaining circuitry is mounted at any convenient location distant from the sample and connected thereto via cable.

Frequency and amplitude stabilized signal generator 42 supplies a test signal to bridge assembly 16, and additionally supplies a reference signal to a controlled rectifier in the conventional apparatus output circuitry represented by block 44. In operation, the output signal from bridge 16 is directly proportional to the moisture of the sampled material when properly corrected for variations in temperature and bulk density. Thus, the output of bridge 16 on lead 46, is amplified by amplifier 48 and directed to conventional output circuitry 44 where the outputs from temperature sensor 20 and bulk density sensor 22 are shaped and multiplied into the bridge output signal in a known manner. The combined signal is amplified and rectified and the resulting DC output signal is read on one or more of several output devices such as indicating meter 50, recorder 52, analog control circuit 54 or A/D converter 56 which would provide an input to other digital devices. The latter two output devices may be used directly for closed loop control.

Where the apparatus includes a plurality of bridge and electrode assemblies, a like number of read out devices, illustrated by gauges 51, are typically provided. Scanning device 58 is synchronized and reset with respect to scanning device 40 by means of timing circuitry 60. Scanner 58 additionally activates sample and hold circuits 206 which provide current to the display devices 51 to maintain a given reading until the next sampling period.

Referring now to FIG. 2, the circuit diagram of the most sensitive part of the disclosed impedance measuring apparatus, the bridge 16, is disclosed. The operation of a bridge is based on the principle that when two sets of impedances are carefully balanced the output signals from these two sets are canceled. Resistors 24 and 28 comprise one leg of the bridge while resistors 26 and 30 comprise the second leg. Sensing electrode 12 is connected between resistors 24 and 26 while a balance impedance comprising capacitor 62 and resistor 64 is connected between resistors 28 and 30. Spark gap 25 is provided to minimize the effects of high voltage discharges to the electrode of the type often encountered when making moisture measurements of relatively dry materials such as paper. Additionally, potentiometer 66 which is connected between resistors 26 and 30 also acts as part of the balance impedance for the sample impedance sensed by electrode 12.

Transformer 14 is the most crucial component of bridge 16 from the point of view of the necessity of its having the highest degree of stability of any of the bridge components. Referring additionally to FIG. 3, transformer 14 is wound with a secondary of low impedance comprising two substantially symmetrical windings 68 and 70. In one embodiment, where the symmetry of windings 68 and 70 was quite close, the output voltages at contacts 72 and 74 were reproducibly symmetrical to better than one part in ten thousand. A transformer constructed in the manner illustrated in FIG. 3, may include a toroidal ferrite core of high permeability on which both the primary coil 76 and secondary coils 68 and 70 are wound. As illustrated in the drawings, all of the coils are wound in a single layer, primary 76 being a nine turn coil, while secondary coils 68 and 70 each include eighteen turns.

One feature of this particular transformer design is that the single layer windings facilitate obtaining the desired symmetrical construction. Each soil 68, 70 and 76 take up a portion of the circumference of the toroidal core proportional to the number of turns of the coil. Primary coil 76 is grounded at one end at 78, while its other end is connected to input cable 80. The ends of the secondary coils 68 and 70 closest to primary coil 76 are grounded at 82, while output terminal 72 and 74 are located adjacent each other at the side of the toroid opposite primary coil 76. In this manner, the cross coupling between primary and secondary coils is minimized. The primary and secondary coils are coupled by the magnetic flux only, and this magnetic flux is extremely uniform within the uncut toroid. Small asymmetries in the parasitic capacities may be neglected for the reason that the impedances of the coils are so low that these capacities do not influence the bridge balance.

The relative closeness of output terminals 72 and 74 of the transformer make it possible to mount bridge resistors 24 and 28 in close thermal contact therewith to equalize thermal drift. Resistors 26 and 30 are mounted in like manner. As the bridge input signals are of opposite polarity, the outputs of resistors 26 and 30 may be directly combined to form one output signal which may be amplified by compensated amplifier 84. Capacitor 86 serves to isolate the DC circuitry of the bridge amplifier from the outside world to prevent low frequency noise pickup such as that caused by an inadvertent contact between the sensing electrode and the 120 V. power line. In a preferred embodiment a capacitor 86 having a value of 1000 pF., 1000 V. has proven to be satisfactory for the above purpose. Silicon diodes 88 are a final precautionary measure and are adapted to short out to ground any signals which are above the 0.3 V. conductance threshold level. For dry sample materials, the bridge output voltage will rarely reach values above 0.1 V., while for materials with high moisture content the resistors 24 and 28 being typically of the order of 500 ohms and resistors 26 and 30 of the order of 1000 ohms will drain off all the high voltage and noise discharges making the diodes redundant.

Use of the instant apparatus to measure relatively small changes in impedance of the sample material requires that the bridge components have stability and drift characteristics at least one order of magnitude better than the components comprising the remainder of the disclosed apparatus. Bridge circuits with a drift stability of 0.1% will be sufficiently reliable for most applications, including the measuring of the moisture content of bulk materials to be discussed with reference to FIGS. 4–6, but moisture measurements of relatively thin sheet material employing the electrode configuration to be discussed with reference to FIGS. 7–9 requires bridge circuits having a stability near 0.02%.

The high order of stability of the disclosed bridge circuit allows for provision of a range offset on the read out apparatus. For example, in measuring the moisture content of wheat without a range offset, an 8% moisture content would read 70% on an appropriate read out meter, while a 15% moisture content would give a full scale reading with the bridge circuit balanced to zero for an empty electrode. Use of the range off-set allows the bridge to be balanced such that the output meter reads 5% for an 8% moisture content and 95% for a 15% moisture content. An additional fine regulation is available by adjusting the variable parameters associated with amplifiers 90 and 92, or the like, illustrated in FIG. 6.

The temperature coefficient of resistors 24, 26, 28 and 30 are matched to track better than $10 \times 10^{-6}$ change in resistance per ° C. over the temperature range in question. The capacitor 62 must also have a low temperature coefficient. Metal film resistors having temperature coefficients down to $25 \times 10^{-6}$ change in resistance per ° C. are available from various sources. Capacitors are also available with temperature coefficients of 20 to $30 \times 10^{-6}$ change in resistance per ° C. Potentiometers 64 and 66 do not require as high a degree of stability for the reason that they contribute a smaller part to the overall impedance. The stability requirement for these elements may be derated in proportion to the degree of their contribution to the overall impedance, which is typically in the ratio of 1 to 10. Thermal stabilities of $1 \times 10^{-4}$ change in resistance per ° C. should thus suffice.

To make a reproducible impedance measurement, the sensing electrode must be adapted to the particular properties of the material to be sampled. One embodiment of a sampling box for free flowing particulate material such as grains, is shown in FIGS. 4 and 5. Sample box 94 has a rectangular cross section, and as illustrated in positioned within a sampling tube 96 having a continuous flow of grain therethrough in a downwardly direction as indicated by arrows 98. Electrode 100 is supported by rods 102 and insulating bushings 104 along the center line of the sampling box. Outlet 106 from the sampling box is slightly smaller in area than material feed outlet 108 formed by converging member 110, and thus sample box 94 is maintained in a constantly fill to overflowing condition by the continuous flow of material through outlet 108. Excess sample material which does not pass through the sample box flows down the conical top portion 112 of the sample box. Top portion 112 is inclined at an angle which is steeper than the normal angle of repose of the sample material funneled thereto which assists in maintaining the sample box filled such that a substantially constant volume of material with a uniform packing density related to the drop height of the grain is obtained. Sample box 94 is, itself, suspended from substantially U-shaped support levers 114 and 116. Referring particularly to FIG. 4, the weight of the material in the sampling box is measured by load cell 22 which is activated through lever 118. The output signal from the load cell is continuous and is proportional to the bulk density of the material sampled. While electrode 100 is mounted substantially along the center line of the sample box, it should be understood that small electrode displacements will not cause a change in the capacitance reading because the larger capacity on one side of the electrode will be compensated by an accordingly smaller capacity on the opposite side.

In one embodiment of the invention, the sample box 94 has been constructed of stainless steel having a relatively low thermal expansion coefficient of $10 \times 10^{-6}$ per ° C., that is a change of $7 \times 10^{-4}$ for a 70° C. change in temperature from $-20°$ C. to $+50°$ C. The capacitance reading is inversely proportional to the distance between the electrode plate and ground, and thus a sample box having a capacitance of 10 pF. is changed by less than 0.01 pF. for a 70° C. change in temperature. This change may be tolerated except for cases where a very low moisture content is to be measured or where the material is fluffy and has a dielectric coefficient very close to one. In this case, the thermal drift may be compensated for by mounting a bimetal strip 120 on one of the support rods of the electrode to provide a small variable capacitance between the bimetal strip and grounded electrode 122. Thermal drift may then be offset by an opposing change of capacitance due to the motion of the bimetal strip. This assembly is protected by a dust cover 124.

An alternative, but more expensive solution is to construct a sample box and electrode from Invar Steel which has a thermal expansion coefficient of only $0.8 \times 10^{-6}$ per ° C. This construction would reduce the thermal drift by a factor of more than ten compared to stainless steel.

In a preferred embodiment, sample box 94 is supported in an upright position by U-shaped arms 114 and 116 which are themselves mounted on the wall of sample tube 96 by means of brackets 126 and 128 respectively. As illustrated, support brackets 126 and 128 comprise short pieces of resilient material such as piano wire mounted to extend between support arms 114 and 116 and the side wall of the sample tube 96 by means of appropriate solder or welded connections. Support arms 114 and 116 are connected at their opposite ends by means of like mountings 130 and 132 to opposite sides of sample box 94. These flexible connections allow sample box 94 to vibrate in the vertical direction. As is best seen in FIG. 5, support arms 114 and 116 have relatively narrow top surface areas thereby reducing dust accumulation thereon which could possibly falsify the weight reading obtained by sensor 22.

Referring again to FIG. 4, a light metal strip 134 is connected between electrode 100 and insulated contact 136 in the outer wall of the sample tube, which contact in turn feeds the bridge assembly 16.

A temperature sensing thermistor 20 is mounted above orifice 108 in contact with the sample material before it drops into the sampling box. Insulated contact 140 feeds this temperature reading to the temperature compensating circuitry discussed hereafter.

The size of the sample box is determined by the size of the material particles to be sampled. For instance, a typical sample box for wheat may have a capacity of 24 cubic inches. The free flowing properties of wheat eliminate the need for additional material handling systems. For other materials such as corn fibers or potato chips additional handling systems would be necessary to compact the material and transport it past the sampling electrode. For the case of wood chips, a sample box must have a capacity of at least 2 cubic feet to average out variations in chip size. Wood chips may be brought to the sample box by means of conveyor or alternatively may be blown in through an air duct. When the sample box is full a reading is taken, the sample box is then emptied by opening a clam shell valve, or the like, at the bottom of the box. For a continuous moisture reading a small conveyor may be installed below the sample box to extract chips at a constant rate. For wood chips, the termal sensor may be installed directly in the sample box, and the box suspended from an overhead load sensing cell by means of wire ropes. Floury or mushy materials may be conveyed by a screw conveyor through a short tubular section containing the electrode which again would have a cross sectional geometry similar to that shown in FIGS. 4 and 5.

Referring now to FIG. 6, a block diagram of the basic circuitry of one preferred form of impedance measuring apparatus suitable for use with the sample box configuration of FIG. 4 is disclosed. Signal generator 42, provides a test signal to the bridge assembly through lead 80 and transformer 14 and at the same time provides a controlling square wave signal to controlled rectifier 144 by means of lead 146. The bridge assembly 16 includes the bridge circuits described with reference to FIG. 2 and amplifier 84. The bridge output voltage which includes the impedance information of the test sample is fed through operational transconductance amplifiers 90 and 92 where correcting factors for temperature and bulk density of the sample are multiplied into the bridge output signal. The combined signal is further amplified and rectified in controlled rectifier 144. The DC output signals on the controlled rectifier is then fed to read out apparatus indicated at 50–56. It will be understood that the DC output signal may be additionally corrected prior to transmission to the read out apparatus by altering the amplification factor, the level bias and the offset voltage to fit the output voltage to the scale of the indicating meter 50, recorder 52, input to an analog control system 54 or analog to digital converter 56 used as an input to other computer circuitry.

A suitable power supply for the disclosed apparatus may include temperature compensated and regulated DC voltages of +10 and −10 volts. It is desirable that voltage level stay constant to within ± 0.1% even in the presence of fluctuations in the supply line voltage of ± 20%.

Lead 80 by which signal generator 42 provides the test signal to the bridge circuit may be a 50 ohm coaxial cable having a length as great as several hundred feet. The test signal typically has a 100 KHz frequency and an RMS voltage of one volt when driving a 50 ohm impedance cable. The harmonic distortion of the signal is well below 1%. Bridge assembly 16 includes ohmic as well as reactive components and thus the bridge balance as well as the phase and voltage of the bridge output signal are frequency dependant. Thus, signal generator 42 is crystal stabilized, and the stabilizing crystals also serve as a filter circuit to reduce the harmonic components of the primary frequency and deliver a clean sinusoidal voltage to the output stages of the signal generator. The output stages are linearized and provide a moderate voltage amplification to deliver a 20 mW signal into the 50 ohm cable. An output transformer like transformer 14 reduces the output impedance of the signal generator which is in the range of 800 ohms down to 50 ohms to match the cable impedance. It will be understood that the transformer input voltage may be further sampled by a diode and rectified to provide a controlling signal to the feedback loop of the oscillator to maintain the ouput voltage constant to one volt ± 0.5%. This feedback control may be temperature compensated.

While not illustrated in the drawings, the square wave signal transmitted on lead 146 to operate controlled rectifier 144 may be generated by directing the signal from signal generator 42 to a transistor having equal resistors in its emitter and collector portions so that the output signals from the emitter and collector are equal in amplitude but inverted in phase. The output signals from the emitter and collector may, in one embodiment, be fed into the two inputs of a sinecosine potentiometer or, simplier, into two paralleled potentiometers the wipers of which are set to act like those of the sine-cosine potentiometer. The outputs from both wipers, after ± 45° phase shifting in a C-R combination are combined and can be set at any phase signal between 0° and 360° relative to the input. This signal may be amplified in three stages of DC coupled PNP and NPN transistors so that a square wave of ± 10 volts is obtained at the output. This output voltage is then averaged by an R-C filter and the resulting DC voltage used to bias the input transistor of an amplifier. The result is a symmetrical output voltage with an average close to zero. Finally, the square wave is inverted and both signals used to operate controlled rectifier 144.

The impedance of relatively dry materials such as wheat or paper is of the order of 300 K ohms and thus the values of the bridge resistors 24, 26, 28 and 30 are in the range of 100 K ohms to 1 M ohms and thus transformer 14 may be considered to operate into an open circuit. Thus, where desired, a large number of similar bridge circuits may be powered from the same transformer without overloading such as illustrated in FIG. 10, for example. The low transformer impedance effectively decouples all of the bridges and allows each bridge to operate without interference from any others. Although not illustrated in FIG. 10, it will be understood that a second transformer identical to transformer 14 may be used to match the 800 ohm output impedance of amplifier 48 to the 50 ohm cable 150 which returns the bridge output signal to the main equipment.

Referring now to FIGS. 7–9, an electrode arrangement suitable for use in measuring the moisture content of very thin sheets of material such as, for example, the entire web of a paper machine having a 12 to 36 foot width. It will be understood that this configuration may also be used to measure moisture content of other thin materials such as fabrics or veneer. In this arrangement, electrodes 152 and ground strips 154 are mounted in a single frame, the electrode being framed on two sides by the ground strips thereby eliminating the need for an additional ground electrode on the opposite side of the material to be measured as was necessary in certain prior art embodiments. As illustrated in FIG. 9, electric fields 156 extend from centrally located electrode 152 to edge placed grounds 154 in an arc extending outwardly from the electrode plane. While electric fields 156 are not homogeneous, the thinness of the material to be measured allows the field to be considered to be relatively homogeneous within the area of interest notwithstanding surface vibrations of the material moving past the electrode. Electrodes 152 and 154 are preferably made from a material having a relatively small thermal expansion coefficient such as stainless steel. These electrodes are embedded in a supporting and insulating layer 158 such that the top surface of the elongate electrode assembly is completely flat. Insulator 158 is mounted on and closes the substantially box shaped support 160 which because of its hollow rigid rectangular cross section performs the multiple functions of supporting the entire electrode assembly across a 10 to 30 foot web of thin material to be measured, as well as protecting the bridge circuits mounted within the closed box to protect them against dust and moisture. In one embodiment, the box support has been completely sealed and continuously flushed with dry air to maintain high impedance level operation of the electric components mounted therewithin. Edge mounted ground strips 154 additionally act to protect insulator 158 and electrodes 152 from damage and abrasion arising from inadvertent contact with the material to be measured.

The capacitance of a 6 inch section of writing paper, for example, is approximately 0.5 pF. For paper having approximately a 7% moisture content, a change in moisture content of ± 1% results in a change in capacitance of 0.01 pF. or less. In order to detect and read this moisture change, the null capacity between electrode 152 and ground 154 which is approximately 5 pF. must be stable to about 0.001 pF.

In earlier designs, attempts were made to balance thermal drift by using a second symmetrical dummy electrode and ground mounted on the back of the active electrode and connected to the other leg of the bridge circuit. The dummy electrode was in thermal equilibrium with the active electrode because both electrodes were mounted on the same piece of glass epoxy printed circuit board or like material having a relatively good thermal conductivity. This type of thermal compensation, however, was unsatisfactory and partially self-defeating in that the gain in better self-compensation for temperature drift was largely offset by the accompanying loss in sensitivity of the equipment.

It has been found that a more effective method of solving this problem is to employ only a single operational electrode 152 and compensate for thermal drift by mechanical means. It will be understood that thermal drift is related in significant part to the expansion or contraction of the insulative material on which the operational and ground electrodes are mounted caused by temperature variation. The electrode null capacitance is primarily the capacitance between electrode 152 and ground strips 154 and box support 160 across the insulative material 158. As the dielectric coefficient of most dielectric material has a negative thermal drift, the capacitance is reduced with rising temperature. Plastic materials also have a rather large expansion coefficient, for example, the expansion coefficient of Teflon is $55 \times 10^{-6}$ while that of epoxy is in the range of 30 to $90 \times 10^{-6}$. Thermal expansion of the insulative material with rising temperature pushes electrode 152 and ground strips 154 further apart thus further reducing null capacitance. Glass fiber laminated epoxy boards of the type used for printed circuits have a thermal expansion coefficient close to that of steel, that is $10 \times 10^{-6}$, and may reduce thermal drift by a factor of 4 or 5, however, for effective use for the disclosed purpose, this thermal compensation factor must be 15 or better. The reason for this high thermal compensation factor may be seen from the fact that the null capacity of a six inch electrode is approximately 5 pF. For a temperature variation of 70° C. between −20° C. and +50° C., the thermal expansion of Teflon is $3.5 \times 10^{-3}$, and thus the change in null capacitance during such a temperature change would be approximately 0.017 pF. The change in capacitance of papers having 2% and 12% moisture contents respectively is in the order of 0.1 pF. and thus a capacitance change of 0.01 pF. must be observed reliably in order to indicate moisture variation in the range between 5% and 10% to within ±0.5% to 1%. Thus, to obtain the desired stability in null capacitance of ± 0.001 pF., the uncompensated drift in capacitance must be reduced by at least a factor of 17, and it has been found that adequate thermal compensation may be obtained by using rods 162 to pull opposing grounded strips 154 which are mounted directly on box 160 toward each other thereby exerting an inward pressure on insulator 158. It has been found that a satisfactory construction material for rods 162 is Invar steel which has a very low thermal expansion coefficient of $0.8 \times 10^{-6}$.

The vertical location of the rods 162 on the sides of box support frame 160 must be determined empirically. The longitudinal spacing of the rods along the electrode assembly, may, as seen in FIG. 7, be at even intervals between successive electrodes where they interfere least with impedance measurement.

Referring particularly to FIG. 9, it will be seen that the upper parts of the side walls of box frame 160 are bent inward at a 90° angle and that the entire box is shaped or welded to form a single frame having a flat bottom surface 164. The insulator and electrode assembly is mounted by means of screws 166 extending through ground strip 154 and insulator 158 into threaded holes in the inwardly bent portions of box frame 160. Fastening means such as cooperating nut and bolt 168 is employed to mount operating electrode 152 on insulator 158.

With an increase in temperature, insulator 158 expands against electrodes 154 which are held against movement by rod 162. The net effect is that an inward pressure is exerted on the insulator generally along the lines defined by arrows 170 and tending to bend insulator 158 inwardly with respect to support box 160 due to its U-shape caused by the inset in which electrode 152 is positioned. This force would also tend to displace electrode 152 inwardly with respect to box 160 and this electrode displacement away from the sheet material being sampled would reduce the impedance measured by the electrode. To compensate for this movement, slots 174 are provided in the insulator along the entire length of the assembly on the lateral sides of electrode 152. Slots 174 provide pivot points which allow the insulator to expand in an outward direction with respect to box frame 160 and it will be understood that the slots must be cut to a depth such that the opposing inward and outward forces compensate each other. Even with slots 174, insulator 158 tends to assert an outward pressure opposing the forces along arrows 170 which tends to pivot the upper portion of the side walls of box 160 about points 176 at which rods 162 are mounted thereby bending the central portion of the side walls inwardly as indicated by arrows 178. This motion is opposed by the thermal expansion of the bottom 164 of the box frame. As the thermal expansion of the steel box is greater than that of the Invar steel rods, a leverage is produced about points 176 which counteract the pressure from the insulator. By optimizing the location of the rods and the depth of slots 174, the electrode assembly may be thermally compensated sufficiently to allow measurement of the moisture content in paper as thin as tissue. In a preferred embodiment of this invention, it has been found that Teflon is a satisfactory insulation material in that it may be formed to run in one continuous piece across the entire electrode assembly to provide a good seal, is non-hygroscopic and has low sticking properties thereby avoiding picking up significant quantities of the dust, starch and moisture carried by paper, for example, which can render an electrode inoperative if deposited on the insulator surface. Additionally, Teflon has sufficient elasticity to give in the directions indicated by arrows 170, and finally, Teflon is easily machinable.

Referring now to FIG. 10, an arrangement whereby one input transformer 14 is employed in conjunction with an array of identical bridge circuits 180 and associated output preamplifiers 182 is illustrated. Bridge circuits 180 may be considered to be identical to the bridge circuit illustrated in FIG. 2 and discussed above. All of the bridge circuits are continuously in operation and the outputs from the various preamplifiers 182 are continually consecutively connected to output amplifier 148.

In earlier U.S. Pat. No. 3,430,140 mentioned above, an electrode arrangement was disclosed where the basic bridge circuits were common and the electrodes were sampled by means of diode switches. This arrangement had several serious drawbacks including the fact that a back biased diode has a residual capacitance of more than 0.1 pF., and thus twenty four diodes added in parallel give a total capacitance of at least 2.4 pF. or one-half of the capacitance of one electrode element. This capacitance varies with the applied bias voltage, and unless this bias voltage is very stable, the cumulative capacitive drift can easily exceed the accuracy required to make the measurement. The electrical characteristics of the diode during conductance is another source of error which cannot be ignored.

In the bridge arrangement disclosed herein, the high impedance portion of the bridge which is also the most sensitive portion of the bridge circuitry is left undisturbed. A complete bridge circuit 180 is employed in conjunction with each sampling electrode, and the sampling itself is done behind the bridge output preamplifier 182. The sampling, therefore does not disturb the operation of either the electrode or the bridge.

One sampling technique uses each of the output preamplifiers 182 as a sampling switch. Only one amplifier is "on" at any one time, and these amplifiers are turned on by their emitter currents which in turn are controlled by BCD to decimal decoders indicated at 184. In one embodiment, BCD to decimal decoders of the type TTL-S.N. 5445 have been used successfully. This BCD to ten line decoder turns on one output line out of ten at any one time as determined by the BCD code.

In the "on" position, the output stage of a decoder allows a current flow of up to 20 mA at a voltage below 0.4 V. In the "off" position, the leakage current is well below 250 $\mu$A even for a voltage of up to 30 V. In the simple switch configuration shown in FIG. 10, the transistor 182 in the "on" position carries a current of 5 mA assuming a value for resistor 186 of 1 k ohm and a negative bus voltage at the decoder of $-5$ V. As illustrated, resistor 188 may typically have a value of 1.5 K ohms and thus causes a drop of 7.5 V. from the +10 V. bus and resulting in a voltage amplification of 1.5. To stabilize this amplification factor, resistors 186 must be accurate to 0.5% and all of the transistors 182 must have a similar amplification factor constant to within ± 10%, that is $\beta$ equals 300 ± 30. A variation in $\beta$ is predominantly offset by the compensating effect of resistors 186. With resistor 186 at 1 K ohm the input impedance seen by the bridge output is about 300 K ohms which is comparatively low.

When as many as forty bridges 180 are assembled in parallel, the sum of the capacitances of all the amplifiers in the "off" state is about 160 pF and the impedance approximately 10 K ohms. This contributes a considerable leakage current compared to the output current from the one amplifier in the "on" state and can significantly falsify the output of the metering system if not controlled. FIG. 11 illustrates a switching technique which results in lower leakage currents and is thus preferable for larger electrode arrays. As was shown in FIG. 10, each individual bridge circuit transistor 182 is connected to resistor 186 and via the common output bus to the output amplifier 48. The input to amplifier 182 is a second transistor 190 which has an input impedance of over 1 M ohms, thus reducing the load on the bridge output. The collector of a third transistor 192 is connected to the emitter of transistor 190, while the base voltage of transistor 192 is provided by resistors 194 and 196 where resistor 194 is biased from + 10 V. and resistor 196 is connected to the switching voltage from the scan control signal.

In the "on" state the voltage at the junction of resistors 186 and 196 is approximately $-5$ V. Transistor 192 is biased via resistor 196 to the off position by a voltage of about $-2$ V. relative to the grounded emitter thereof, while transistor 182 is conducting so that the signal from the bridge output is directly transferred to the output amplifier 48 via transistors 190 and 182. In the "off" state, the voltage at the junction of resistors 186 and 196 is nearly zero. Transistor 182 is non-conducting because its base and emitter are at about the same voltage. Transistor 192 is biased "on" by the current from resistor 194 and in this way any of the leakage current from the bridge bypassed through the capacitance of transistor 190 is grounded out via transistor 192 and never reaches the output bus. Output amplifier 48 is well stabilized. The bridge output voltage is amplified to about 1 V. and then matched to the 50 ohm cable impedance by means of transformer 14. This ensures a strong signal level so that noise pickup in the signal cable which may be several hundred feet long is negligible.

Shaping or amplitude modulating of the bridge output voltage is necessary to correct for variations in temperature and bulk density. The temperature of the sample material may be obtained from a sensor 20 (FIG. 4) normally located at the boundary of the material flow close to the sampling space. A thermistor is a convenient temperature probe, in that it has a short time response and may be supplied with an average resistance of about 100 K ohms which makes it ideal for use as an input to operational amplifier 198. By varying the amplifier parameters, the output voltage range may be adjusted as desired to read a convenient temperature range. As the operational amplifier has a low output impedance, it may be used to directly drive the cable from the bridge assembly to the remainder of the equipment.

With regard to correcting for variations in bulk density, the weight of a fixed volume of material may be determined by use of a load cell 22 (FIGS. 4 and 6). Load cell 22 is connected to the inputs of an operational amplifier 200 and the range of output voltage is adjusted to read directly either bulk density or total weight as desired.

The calibrated temperature and bulk density outputs may then, as mentioned earlier, be multiplied into the output of the bridge circuit through the use of so-called operational transconductance amplifiers (OTA) 90 and 92. OTAs which have been found suitable for this purpose include CA 3080 from RCA. In combining the temperature and bulk density outputs with the bridge circuit output, it should be remembered that the temperature and bulk density outputs are not absolute values, but rather relative values and thus the weighting factors or slope dependants of temperature and bulk density must be found empirically relative to some main operating point, and these factors are then programmed into this system by adjusting a set of voltage dividers 202 and 204. A like programming result could also be achieved by changing the gain and offset of amplifier 90 and 92, but it would not then be possible to also provide a metered read out for both temperature and bulk density.

The transconductance and hence amplification factor of a typical OTA changes by a factor of $-2$ for a temperature change of 180° from $-55°$ C. to $+125°$ C. This is a change in the amplification factor of $-1.1\%$ per degree centigrade. It will be understood that a resistor network with a thermistor in series may be used to change the bias current by a compensating factor of $+1.1\%$ per degree centigrade to correct for the temperature drift of the OTA. As discussed previously, the temperature coefficient of an impedance measurement of, for example, wood chips may be drastically different for temperatures above and below the freezing point. The temperature compensation thus must be sufficiently complex to compensate for the various slope dependencies. This may be achieved by installing a resistor network comprised of one or more voltage dividers 202 (FIG. 6) depending on the number of differing slopes M/T required to eliminate the thermal dependence of the impedance M over the required range of temperature T. Each one of the voltage dividers has a characteristic impedance and is switched by a diode to the bias current input of amplifier 92. Each diode turns on at a given temperature related output voltage of amplifier 198. When a diode is turned on a bias current is added to or subtracted from the already existing bias current. The amount of additional bias current is determined by the voltage and impedance of the voltage divider and the particular diode. Each voltage divider is properly adjusted to make the output of OTA 92 independent of temperature over a partial temperature range until it becomes necessary to correct for a new slope dependence by switching on another diode.

The corrected signal from the temperature and bulk density multiplier circuits is then fed to controlled rectifier 144, which, as discussed above, receives a controlling square wave signal from oscillator 42 by means of cable 146. The frequency of this square wave is the same as that of the bridge output signal and its phase may be set to accept either ohmic or capacitance components of the bridge output signal or a combination of both representing the complex impedance. Controlled rectifier 144 filters out incoherent signals and reduces contributions from higher harmonics which pass the bridge circuitry. Finally, the DC output signal from the controlled rectifier 144 may be fed to an operational amplifier where small adjustments in amplification and offset may be made such that the output signal is properly calibrated to drive one or more of the output devices 50, 52, 54 or 56.

Referring again to FIG. 1, a means whereby the individual bridges of an array could separately and repeatedly be sampled has been discussed. In order to make such a sampling technique feasible, each metering device must be synchronized with its corresponding bridge circuit and hence as many metering circuits are required as there are bridge and electrode elements such as 16, 32, 34, 36 and 38.

During the time when a particular bridge element is sampled, the corresponding meter is turned on and connected to the output circuitry by means of a sample and hold circuit indicated at 206 (FIG. 1). The OTA described above, may also be used as a sample and hold circuit. The sample hold circuit is activated by the bias current to the OTA and the current is turned off to hold the sampled value. The bias current to the OTA may be provided by a BCD to Decimal decoder identical to that described previously for controlling the bridge samplers. Two identical BCD to Decimal decoders represented by elements 40 and 58 (FIG. 1) may be employed to activate both the scanner for the moisture measurement and the sample hold circuits 206. Decoders 40 and 58 are synchronized by timing device 60. Up to ten bridge or meter elements may be switched by a single decoder unit using all four of the ABCD inputs of the BCD code. Three decoder units may cover up to twenty four bridge or meter elements using the first eight outputs of each unit operated by the repeated count one to eight. Input D of each decoder goes to a separate logic line and is used to activate only one decoder at a time.

Figure 12:
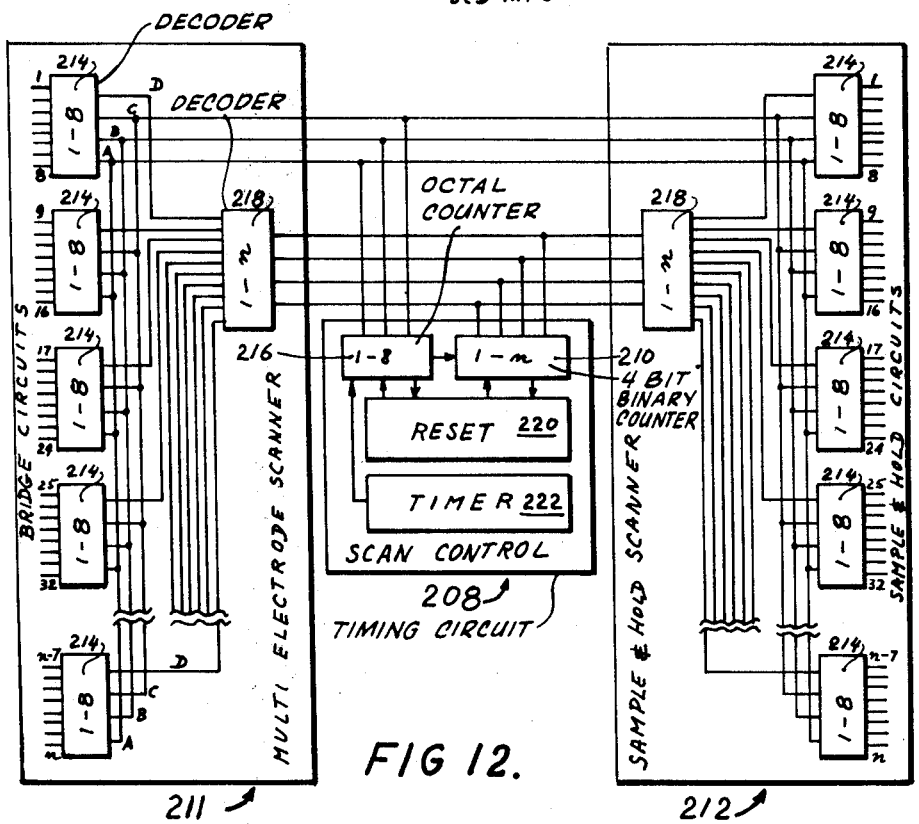
FIG. 12 is a schematic diagram of typical logic circuitry of the present invention used to sample and display a plurality of electrode readings.

FIG. 12 is a logic diagram for an eighty element scanning array including the timing circuit generally indicated at 208 and identical decoder units 211 and 212. As illustrated, identical decoders 214 each controlling eight elements are in turn controlled by a common input code ABC from an octal counter 216. In one embodiment, a four bit binary counter where only the first three code outputs ABC were used was employed as an octal counter.

The fourth input D to each of the decoders 214 is used as a logic signal to turn on only one decoder at a time. Where only three decoders are employed, they may be controlled by a set of three input lines connected to inputs D directly from counter 210. Where three to ten decoders are employed additional decoders 218 are added in each unit 211 and 212 which act via the D inputs to turn on the various decoders one through ten in consecutive order. Decoders 218 are controlled by a four bit binary counter 210 adapted to use as many as all four of the input lines depending on the number of decoders to be switched. Using all eight outputs from counters 216 and 210 consecutively to drive four decoders 218 allows as many as 255 separate bridge electrodes to be controlled, which arrangement should suffice for even the most elaborate scanning electrode arrangement.

After scanning the array of N elements, the counters and decoders are reset to zero by means of reset circuit 220 which is triggered when counters 216 and 210 reach the number $N + 1$ to start a new cycle. A nand-gate with the appropriate number of inputs, varying from three to eight depending upon the number of decoders, produces a reset pulse which is returned to counters 216 and 210. The timer 222 consists of a unijunction transistor which generates pulses of the desired frequency to drive counter 216, which in turn drives counter 210.

An "on" period of one hundred cycles of the basic test frequency should let the bridge and output circuitry reach equilibrium conditions. For a 100 KHz test frequency and an electrode with 40 elements, this means that the scanning rate can be as high as 25 scans per second. Usually however a scanning rate of one to 2 scans per second will result in improved filtering of the output signal which may be particularly important when cable noise is present.

The invention may be embodied in other specific forms without departing from the spirit or central characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

What is claimed is:

1. A measuring apparatus including:
   signal generating means providing a sample signal of a certain frequency and phase;
   sensing circuit means connected to said signal generator means and having an output signal, said output signal having a phase related amplitude which is proportional to the impedance of the sample of material;
   temperature sensor means monitoring the temperature of a portion of said sample of material and having an electrical output;
   first signal shaping circuit means converting the output of said temperature sensor means to an output signal having a temperature related dependence; and,
   second signal shaping circuit means combining the output signals of said sensing circuit means and said output signal of said first signal shaping circuit means thereby correcting the phase related amplitude signal of said sensing circuit for temperature related variations.

2. The measuring apparatus of claim 1 wherein said sensing circuit means measures the capacitive component of the impedance of the sample of material.

3. The measuring apparatus of claim 1 wherein said sensing circuit means measures the resistive component of the impedance of the sample of material.

4. The measuring apparatus of claim 1 wherein said temperature sensor means includes a thermistor having an electrical output and wherein said first signal shaping circuit means includes operational amplifier means amplifying the output of said thermistor.

5. The measuring apparatus of claim 1 wherein said second signal shaping circuit means includes a multiplier circuit.

6. The measuring apparatus of claim 5 wherein said multiplier circuit includes an operational transconductance amplifier.

7. An impedance measuring apparatus including:
signal generator means providing a sample signal of a certain frequency and phase;
sensing circuit means connected to said signal generator means and having an output signal, said output signal having a phase related amplitude which is proportional to the impedance of the sample of material;
said sensing circuit means including electrode means sensing the impedance to be measured, said electrode means including an electrode mounted within and electrically isolated from a grounded sample box;
bulk density measuring means monitoring the bulk density of the material within said sample box and having an electrical output;
signal shaping circuit means converting the electrical output of said bulk density measuring means to an output signal having a bulk density related dependence; and,
multiplier circuit means combining the output signals of said sensing circuit means and said bulk density signal shaping circuit means.

8. The impedance measuring apparatus of claim 7 wherein said sensing circuit means is sensitive to the capacitive component of the impedance of the sample of material.

9. The impedance measuring apparatus of claim 7 wherein said sensing circuit means is sensitive to the resistive component of the impedance of the sample of material.

10. The impedance measuring apparatus of claim 7 wherein said bulk density measuring means includes a load cell having an electrical output measuring the weight of a constant volume of material within said sample box;
an operational amplifier amplifying the output of said load cell; and,
said multiplier circuit means comprising an operational transconductance amplifier.

11. Impedance measuring apparatus including:
signal generator means providing a sample signal having a certain frequency and phase;
sensing circuit means connected to said signal generator means and having an output signal, said output signal having a phase related amplitude which is proportional to the impedance of the sample of material;
temperature sensor means monitoring the temperature of a portion of said sample of material and having an electrical output;
first signal shaping circuit means converting the output of said temperature sensor means to an output signal having a temperature related dependence;
bulk density measuring means monitoring the bulk density of said sample of material and having an electrical output;
second signal shaping circuit means converting the output of said bulk density measuring means to an output signal having a bulk density related dependence; and,
multiplier circuit means combining the output signals of said sensing circuit means, said first signal shaping circuit means, and said second signal shaping circuit means to correct the output signal of said sensing circuit means for temperature and bulk density related variations.

12. The impedance measuring apparatus of claim 11 wherein said impedance sensing circuit means is sensitive to the capacitive component of the impedance of the sample of material.

13. The impedance measuring apparatus of claim 11 wherein said impedance sensing circuit means is sensitive to the resistive component of the impedance of the sample of material.

* * * * *